US005250044A

United States Patent [19]

Irr et al.

[11] Patent Number: 5,250,044

[45] Date of Patent: Oct. 5, 1993

[54] BLOOD CRYOPRESERVATION CONTAINER

[75] Inventors: Joseph D. Irr, Newark; John D. Walker, New Castle, both of Del.

[73] Assignee: Du Pont Merck Pharmaceutical Company, Wilmington, Del.

[21] Appl. No.: 475,604

[22] Filed: Feb. 6, 1990

[51] Int. Cl.[5] ........................ A61B 19/00; A61M 5/32

[52] U.S. Cl. ........................ 604/403; 604/415

[58] Field of Search ................ 604/403, 408, 411, 415

[56] References Cited

U.S. PATENT DOCUMENTS

| | | | |
|---|---|---|---|
| 3,137,438 | 6/1964 | Milton . | |
| 3,337,117 | 8/1967 | Lehmacher et al. . | |
| 3,576,650 | 4/1971 | Underwood et al. | 604/408 X |
| 3,746,001 | 7/1973 | Ralston, Jr. | 604/408 |
| 3,942,529 | 3/1976 | Waage . | |
| 4,018,911 | 4/1977 | Lionetti et al. . | |
| 4,131,200 | 12/1978 | Rinfret . | |
| 4,198,972 | 4/1980 | Herb | 604/408 |
| 4,212,299 | 7/1980 | Yokokoji et al. | 604/408 |
| 4,322,298 | 3/1982 | Persidsky . | |
| 4,365,629 | 12/1982 | Pert et al. | 604/408 |
| 4,482,585 | 11/1984 | Ohodaira et al. . | |
| 4,496,362 | 1/1985 | Leurink | 604/415 X |
| 4,505,708 | 3/1985 | Gajenski et al. | 604/403 X |
| 4,596,573 | 6/1986 | Donnan et al. | 604/415 |
| 4,723,956 | 2/1988 | Schnell et al. . | |
| 4,976,708 | 12/1990 | Oshiyama | 604/408 |
| 4,994,057 | 2/1991 | Carmen et al. | 604/403 X |

FOREIGN PATENT DOCUMENTS

| | | |
|---|---|---|
| 823030 | 9/1969 | Canada . |
| 8904280 | 5/1989 | PCT Int'l Appl. . |

*Primary Examiner*—David J. Isabella
*Assistant Examiner*—Elizabeth M. Burke
*Attorney, Agent, or Firm*—Blair Q. Ferguson; Margaret A. Horn; Gildo E. Fato

[57] ABSTRACT

This invention relates to bags for the cryopreservation of mammalian cells and particularly for the long-term freezing of red blood cell. This invention also relates to methods of manufacturing such bags.

11 Claims, 4 Drawing Sheets

BLOOD CRYOPRESERVATION CONTAINER

FIELD OF THE INVENTION

This invention relates to novel containers for the storage of mammalian cells and particularly for the long term cryopreservation of red blood cells.

BACKGROUND OF THE INVENTION

This invention relates to an improved container for the cryopreservation of mammalian cells and particularly for the long-term cryopreservation of red blood cells. The cryopreservation, or freezing, of red blood cells is a relatively recent development in the medical area. One of the processes used for the freezing of red blood cells is described in U.S. Pat. No. 4,018,911 which describes a method of freezing red blood cells using hydroxyethyl starch (HES). This patent however, does not address the problems associated with providing an appropriate blood compatible bag which incorporates the particular characteristics needed for freezing with liquid nitrogen.

One commercially available bag for cryopreservation of blood components is made by Gambro. Its utility for red blood cell cryopreservation is limited, however, because the spike ports protrude and can be damaged at liquid nitrogen temperatures. The presence of these parts usually requires these bags to be stored in metal containers, thereby using valuable space in the storage cabinets. If one removes the protruding parts at any time, the integrity of the bags content is compromised.

Ideally, a container or bag for cryopreservation in liquid nitrogen should have a number of properties. It should 1) not break or leak at any time during the process, 2) allow for rapid, easy insertion and removal of a spike during transfusion, 3) provide a flat transfusion port so that a large quantity of these containers can be stored without requiring a lot of additional space, and 4) all spike ports, including the transfusion port should be designed in such a manner as to eliminate protrusions which could break off at low temperatures during handling. In addition, since the containers will be stored in liquid nitrogen, it should have low nitrogen permeability and good low temperature properties.

SUMMARY OF THE INVENTION

The present invention provides a container suitable for the cryopreservation of mammalian cells, prepared using thermoplastic films which afford the advantages of medical storage bags previously available for the cryopreservation of cells, combined with the advantage of a flat transfusion port tab insert which allows a large number of these bags filled with blood, to be stacked one on top of another for freezing. In addition, the resilient nature of the spike-through material used in the transfusion port tab insert provides a means for holding in place a spike inserted into the port for the transfusion of red blood cells to the patient.

Specifically, the instant invention provides, in a container comprising a body made from one or more layers of thermoplastic film material (3), a filling port (2) and an transfusion port sealed between said layers, the improvement comprising the transfusion port being incorporated into a transfusion port tab insert (1) comprising:

(a) one or more thermoplastic film layers (10) bondable on one side to the inside of the body of the container;

(b) one or more strips of spike-through material (12) bondable on one side to the inside of the thermoplastic film (10), said spike-through or puncturable material having a high degree of resilience; and (c) one or more nonbondable strips of material (11) being non-bondable to the spike-through material (12);

wherein the thermoplastic film strips (10) are bonded by peripheral seals (13) made on each side of the tab insert (1) such that the spike-through material (12) is sealed to itself, except to the extent that the nonbondable strip of material (11) prevents such bonding, and the thermoplastic film (10) is sealed to the spike-through material (12) and optionally an additional seal is made across the width of the spike port tab insert (1) perpendicular to the peripheral seals (13).

Preferably, the spike-through or puncturable material (12) is a highly resilient material such as a thermoplastic polyester which provides a means for holding a spike inserted therein in place during the transfusion of red blood cells and which provides a liquid-tight seal around such inserted spike.

In another embodiment of this invention a specified amount of HES is placed in the bag during manufacture via the filling port, this filling port being optionally removable, and preferably removed, after cells and HES are added to the bag and before cryopreservation thereof.

DETAILED DESCRIPTION

Figure 1:
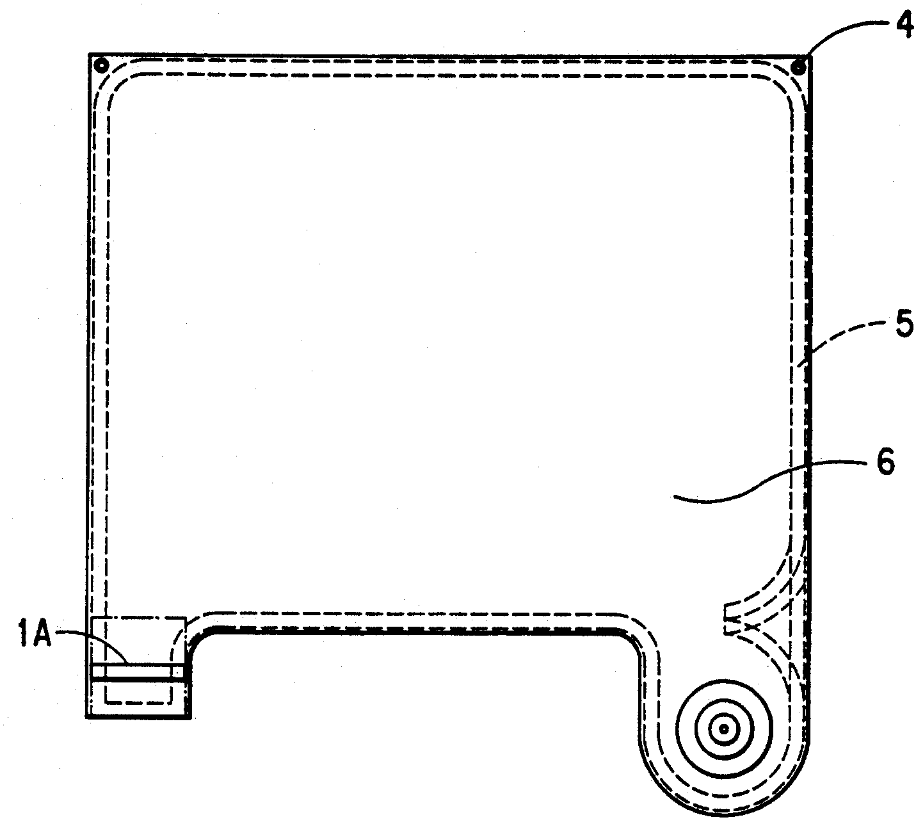
FIG. 1 is a plan view of a flexible bag utilizing the invention of this application.

There is provided a container comprising a body including an outside and made from one or more layers of thermoplastic film material (3), a filling port (2) and an transfusion port sealed between said layers, the improvement comprising the transfusion port being incorporated into an transfusion port tab insert (1) comprising:

(a) one or more thermoplastic film strips (10) bondable on one side to the inside of the body of the container;

(b) one or more strips of spike-through material (12) bondable on one side to the inside of the the thermoplastic film (10), said spike-through material having a high degree of resilience; and (c) one or more nonbondable strips of material (11) being non-bondable to the spike-through material (12);

wherein the thermoplastic film strips (10) are bonded by peripheral seals (13) made on each side of the tab insert (1) such that the spike-through material (12) is sealed to itself, except to the extent that the nonbondable strip of material (11) prevents such bonding, and the thermoplastic film (10) is sealed to the spike-through material (12) and optionally an additional seal is made across the width of the spike port tab insert (1) perpendicular to the peripheral seals (13).

Referring to the FIGS. 1 through 7, several embodiments of the invention are disclosed. The container or bag is made of one or more sheets of thermoplastic film (3) which are sealed together peripherally. The preferred film is a laminate film having a first layer of a polyimide core coated or laminated with a second layer comprising a fluoropolymer, for example a laminate film such as Kapton ®FN, commercially available from E. I. du Pont de Nemours, which is a polyimide film coated with Teflon ® FEP. The seals (5) are preferably made using a thermal impulse sealer such as those commercially available from Vertrod Corporation. Additionally, other means of sealing such as with lasers, or indirect radio frequency sealers, may be used. Seals can be from about 0.032 to about 0.75 inches wide and preferably are about 0.25 inches wide and can be more than one seal in parallel. Seals in the corners of the bag are preferably made with a large (typically 1 inch) radius to reduce mechanical stress in the corners and to reduce areas of the bag in which red blood cells will not survive.

The top of the container may carry other peripheral seals and one or more suspension holes (4) for hanging the bag during usage. In a preferred embodiment, the bag is filled during manufacture with a starch solution (6) in an amount sufficient for the cryopreservation of red blood cells.

Figure 2:
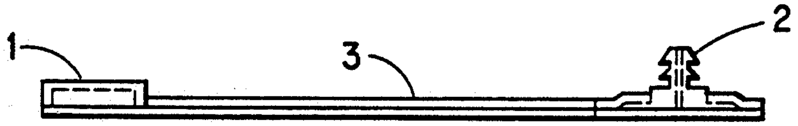
FIG. 2 is a side elevational view of the container of FIG. 1.
Figure 6:
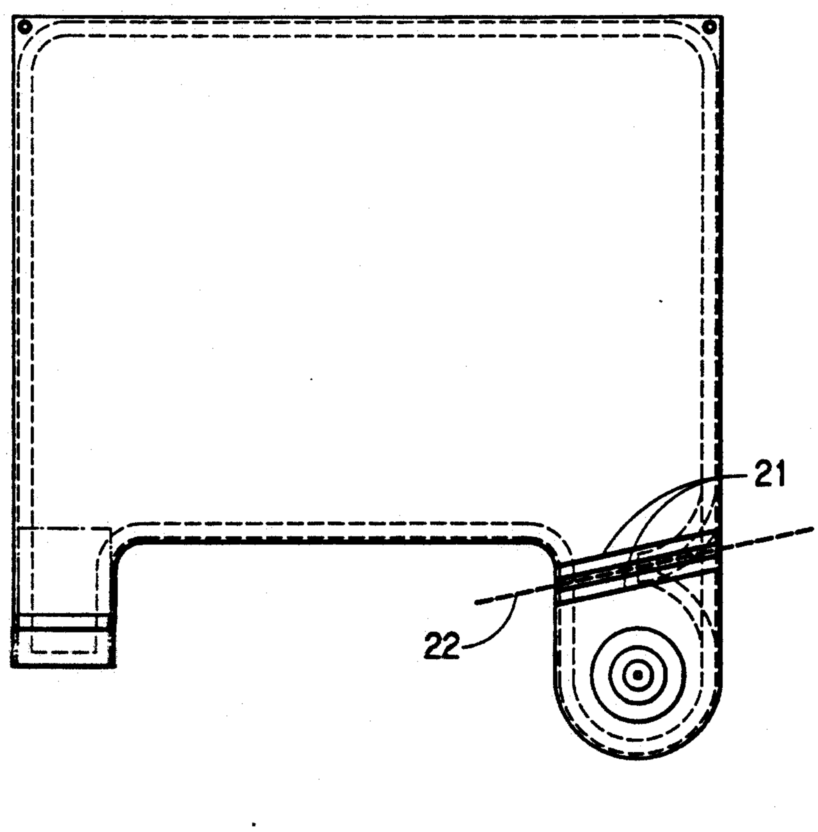
FIG. 6 is a plan view of the bag filled with HES and blood, prior to draining.
Figure 7:
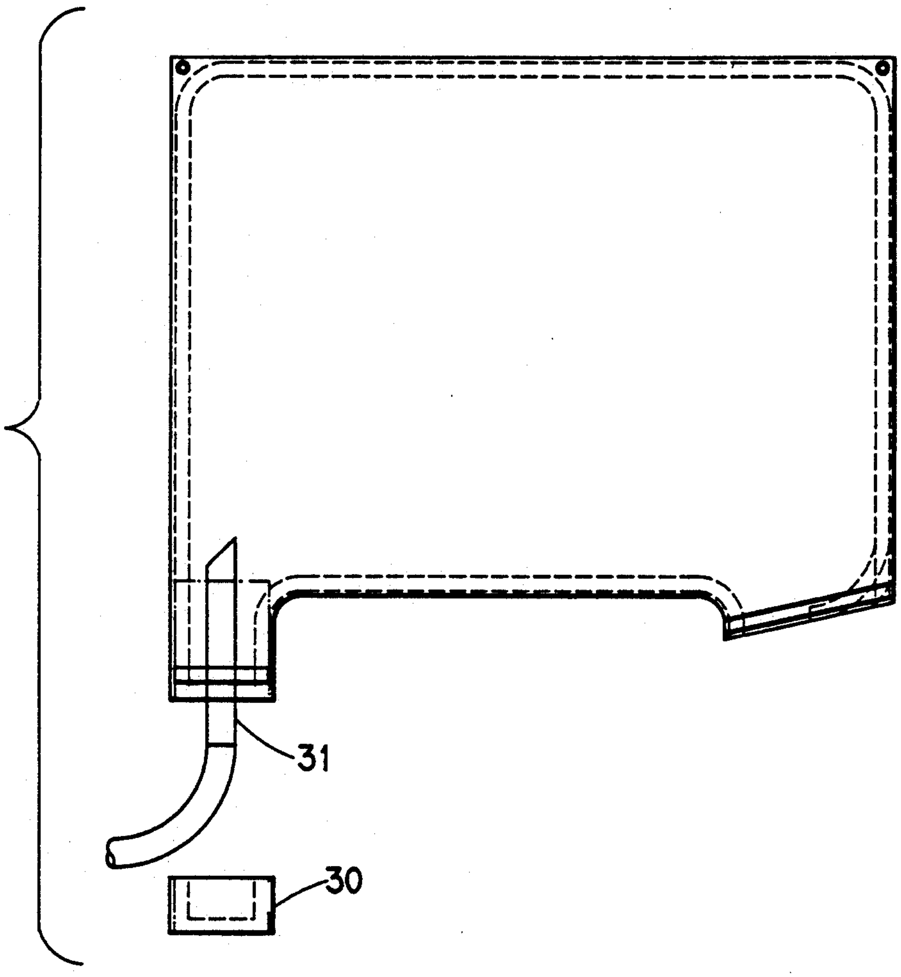
FIG. 7 is a plan view of the bag post-filling with HES and red blood cells and post freezing and thawing with a transfusion spike inserted therein.

As shown in FIG. 2, a filling port (2) is a molded port protruding from the bag for the filling of the bag with starch solution during manufacture and red blood cells by user. This filling port must have a sealing means such as sealed tubing connected to it so that a closed system is provided. Other means for closing the system at the filling port (2) are within those known to people skilled in the art. This filling port (2) is optionally removable by the user as shown in FIGS. 6 and 7. Prior to removal, the user must use any commercially available bar sealer to place filling port tab removal seals (21) across the filling tab. The filling port may then be removed by cutting at the filling port removal location (22) between the seals (21). The port (2) is preferably made of Teflon ® FEP or PFA, preferably injection-molded. The port has a through-hole for passage of starch and red blood cells and a wide flange at the base which is bonded to the inside of the bag. The top of the port extends outside the bag through a hole in the bag film larger than the diameter of barbs (2A) thereon but smaller than the flange diameter. The port (2) has one or more barbs (2A) for holding tubing placed on the port, the tubing being held onto the barb(s) preferably by mechanical press-fit, although adhesives may be used.

Figure 3:
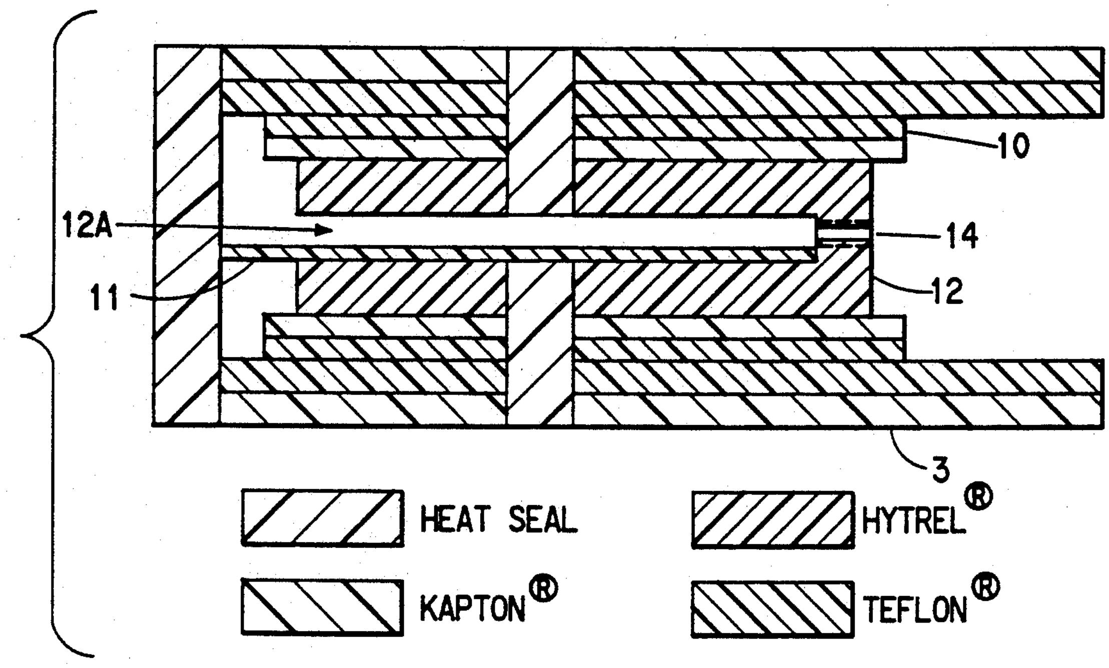
FIG. 3 is a fragmentary, cross-sectional view of the spike port tab insert sealed within the bag of FIGS. 1 and 2.
Figure 4:
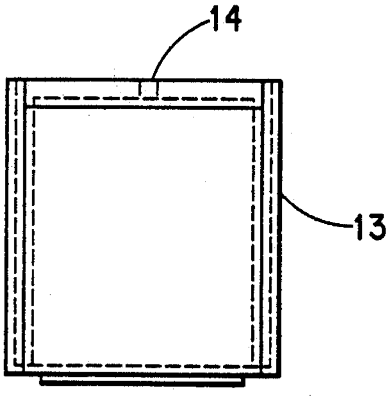
FIG. 4 is a plan view of the spike port tab insert.
Figure 5:
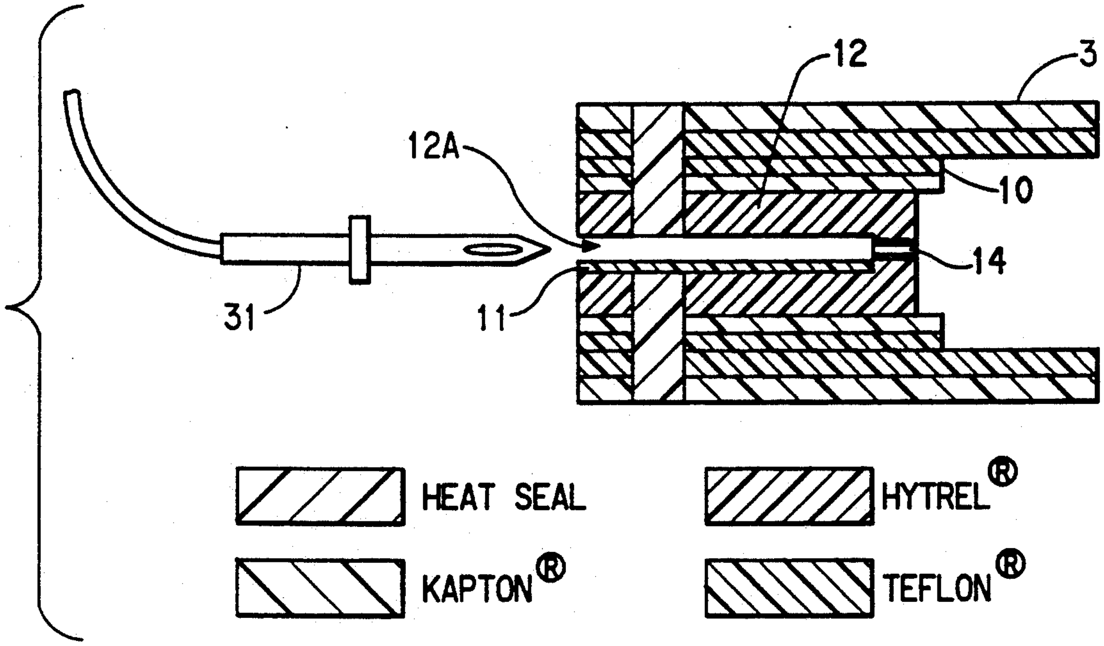
FIG. 5 is a fragmentary, cross-sectional view of the spike port tab insert sealed within the bag of FIGS. 1 and 2 and having a transfusion spike inserted therein.

Referring to FIGS. 3 through 5, the spike port tab insert (1) is sealed within the layers of thermoplastic film comprising the body (3) of the bag. The spike port tab insert (1) comprises one or more layers of a thermoplastic film strip (10) which is preferably a double-bond film such as Kapton ®FN, which is bondable on one side to the inside layer of the thermoplastic film (3) for example a Teflon ® to Teflon ® bond, and which is bondable on the other side to the spike-through material (12). The films (10,12 and 3) being sealed peripherally (13) on each side of the spike port tab insert such that the spike-through material (12) is sealed to itself, except to the extent the non-bondable layer (11) prevents such bonding, and that the inside of the thermoplastic film (10) is sealed to the spike-through material (12) and the outside of the thermoplastic film (10) is sealed to the inside of the thermoplastic film (3) comprising the body of the bag. The nonbondable strip (11) prevents the spike-through (12) material from bonding to itself during manufacture. The nonbondable strip (11) is preferably Teflon ®FEP although other fluoropolymers and other polymers and metal that do not bond to the spike-through material (12) will work. The material (11) can be from about 0.0005 to about 0.010 inches thick, preferably about 0.002 inches thick. This material (11) remains inside the port and is slightly smaller in width than the spike-through material (12) so that the spike-through material (12) can bond to itself at the outer most edges but will not otherwise bond to itself, thereby providing a channel (12A) for the insertion of a spike.

The spike-through material (12) is preferably a thermoplastic polyester elastomer such as Hytrel ® which is commercially available from E. I. du Pont de Nemours and Company. The advantage of using a film such as Hytrel ® which is a resilient polyester is that its resilient nature provides a means for holding any spike port inserted therein in place during the transfusion of red blood cells from the bag to the patient. In addition, it will create a liquid-tight seal around an object, such as a spike inserted into the spike-through material (12) or Hytrel ® layer. Further properties of Hytrel ® which make it preferable in the present invention are that it is autoclavable and it is red blood cell compatible.

In a preferred embodiment of the present invention a single layer of polyester elastomer film such as Hytrel ® is folded inside the thermoplastic film strip layers (10) of the spike port tab insert. The spike-through material (12), preferably Hytrel ® is sealed to layers (10) along the sides of the insert tab (13) providing a channel (12A) through which a spike port can be inserted. As shown in FIGS. 3 and 4, prior to using the bag, a cut must be made by the user to provide access to the channel (12A) which is sealed off during manufacture to provide a closed system. As shown in FIGS. 3, 5 and 7 a cut is made in the spike port tab at the end opposite the spike insertion point (14). This cut provides access to the channel (12A) for the insertion of a spike (31). A portion (30) of the spike port tab is removed after the cut is made and is discardable in compliance with biohazardous waste removal practices. At the folded portion of the spike-through layer(12), which is adjacent to the interior of the container, is provided a spike insertion point (14) which predisposes layer (12) to penetration by any spike inserted therein. The spike insertion point (14) can be made by means known to those skilled in the art, including providing a small hole in the layer (12) or by thinning the spike-through material (12) at this point or by creating perforations in the spike-through material (12) at this point. Preferably any spike insertion point (14) is placed at the center of the width of the spike-through material (12). Any spike insertion point is preferably smaller than the diameter of any spike to be inserted therein. The characteristics of Hytrel ®, particularly its resilient nature will cause a liquid-tight seal to be formed around any spike inserted therein, thus preventing any leakage of the red blood cells stored in the bag, during the transfusion of such red blood cells into a patient. This will prevent not only loss of the limited red blood cell supply, but also will reduce the likelihood of medical personnel being exposed to spilled red blood cells which may carry infectious diseases.

What is claimed is:

1. A container for the cryopreservation of mammalian cells comprising a body formed of at least one thermoplastic film material and including an inside, a filling port positioned in the container body and a transfusion port sealed to the container body, the improvement comprising a transfusion port tab insert, said insert including a puncturable seal and comprising (a) at least one thermoplastic film strip bondable on one side thereof to the inside of the body of the container and bondable on the other side to the puncturable seal, the strip including edges which are sealed together to encompass the puncturable seal;

(b) at least one strip of puncturable material forming a puncturable seal including a channel for receiving a spike for transfusion of the contents of the container, the puncturable seal including a spike insertion point, puncturable by a spike when the spike is inserted in the channel and wherein the puncturable seal is one strip of polyester elastomer film folded over on itself;

(c) at least one film of material positioned within the channel of the puncturable seal, said film being non-bondable to the puncturable material to thereby prevent the puncturable material from bonding to itself and closing the channel in the puncturable seal; said transfusion port tab insert being sealed at the end distal from the container body to thereby seal the insert and channel and thereby prevent contamination of the container or leakage of any mammalian cells stored within the container.

2. A container of claim 1 wherein the polyester elastomer film is about 0.0005 to about 0.060 inches thick.

3. A container of claim 3 wherein the polyester elastomer film is about 0.005 inches thick.

4. A container of claim 3 wherein the spike insertion point (14) includes perforations in the polyester elastomer film.

5. A container of claim 1 wherein the spike insertion point (14) comprises thinner puncturable material (12) at the insertion point.

6. A container of claim 1 wherein the spike insertion point (14) comprises a hole having a diameter of about 0.01 to about 0.25 inches.

7. A container of claim 6 wherein the hole has a diameter of about 0.06 inches.

8. A container of claim 1 wherein the filling port (3) is removable prior to cryopreservation of the container and mammalian cells therein.

9. The container of claim 1 wherein the thermoplastic film strip bondable on one side to the inside of the body of the container and on another side to the puncturable seal comprises a laminate including a first layer of a polyimide core and a second layer of a fluoropolymer.

10. The container of claim 9 wherein the film of material positioned within the channel of the puncturable seal comprises a fluoropolymer film.

11. The container of claim 1 wherein the puncturable material forming the puncturable seal is a thermoplastic polyester elastomer.

* * * * *